(12) United States Patent
Ikemoto

(10) Patent No.: US 10,406,151 B2
(45) Date of Patent: *Sep. 10, 2019

(54) METHOD OF INDUCING AUTOPHAGY

(71) Applicant: Mitsubishi Gas Chemical Company, Inc., Chiyoda-ku (JP)

(72) Inventor: Kazuto Ikemoto, Niigata (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/817,509

(22) Filed: Nov. 20, 2017

(65) Prior Publication Data

US 2018/0147200 A1    May 31, 2018

(30) Foreign Application Priority Data

Nov. 25, 2016    (JP) ................... 2016-229146

(51) Int. Cl.
| | |
|---|---|
| *A61K 31/4745* | (2006.01) |
| *A61P 29/00* | (2006.01) |
| *A23L 33/10* | (2016.01) |
| *A61P 25/00* | (2006.01) |

(52) U.S. Cl.
CPC .......... *A61K 31/4745* (2013.01); *A23L 33/10* (2016.08); *A61P 25/00* (2018.01); *A61P 29/00* (2018.01)

(58) Field of Classification Search
CPC ... A61K 31/4745; C07D 471/04; A23L 33/10; A61P 25/00; A61P 29/00
See application file for complete search history.

(56) References Cited

U.S. PATENT DOCUMENTS

| | | | | |
|---|---|---|---|---|
| 5,589,481 A * | 12/1996 | Tsuji | ............ | A61K 31/47 514/287 |
| 5,846,977 A * | 12/1998 | Tsuji | ............ | A61K 31/47 514/292 |
| 8,575,190 B2 * | 11/2013 | Kamimura | ............ | C07D 471/04 514/292 |
| 8,946,423 B2 * | 2/2015 | Ikemoto | ............ | C07D 471/04 546/84 |
| 9,163,014 B2 * | 10/2015 | Edahiro | ............ | C07D 471/04 |
| 9,321,770 B2 * | 4/2016 | Edahiro | ............ | C07D 471/04 |
| 9,695,164 B2 * | 7/2017 | Zhu | ............ | C07D 471/04 |
| 10,053,459 B2 * | 8/2018 | Mori | ............ | A61K 31/4745 |
| 2010/0190815 A1 * | 7/2010 | Ogino | ............ | A61K 31/437 514/292 |
| 2012/0323009 A1 * | 12/2012 | Ikemoto | ............ | C07D 471/04 546/84 |
| 2015/0272881 A1 * | 10/2015 | Ikemoto | ............ | A61K 9/06 514/292 |
| 2016/0039816 A1 | 2/2016 | Edahiro et al. | | |

FOREIGN PATENT DOCUMENTS

| | | |
|---|---|---|
| JP | 2007-143452 | 6/2007 |
| WO | WO 2011/007633 A1 | 1/2011 |

OTHER PUBLICATIONS

Urakami et al., "Synthesis of esters of coenzyme PQQ and IPQ, and stimulation of nerve growth factor production", 1995/1996, BioFactors, 5(3), pp. 139-146. (Year: 1995).*

Mukai et al., "Kinetic Study of the Quenching Reaction of Singlet Oxygen by Pyrroloquinolinequinol (PQQH2, a Reduced Form of Pyrroloquinolinequinone) in Micellar Solution", 2011, J. Agric. Food Chem., 59(5), pp. 1705-1712. (Year: 2011).*

Gong et al., "Effect of pyrroloquinoline quinone on neuropathic pain following chronic constriction injury of the sciatic nerve in rats", 2012, European J. Pharmacology, 697(1-3), pp. 53-58. (Year: 2012).*

Tsukakoshi et al., "Esterification of PQQ Enhances Blood-Brain Barrier Permeability and Inhibitory Activity against Amyloidogenic Protein Fibril Formation", 2018, ACS Chem. Neurosci., 9(12), pp. 2898-2903. (Year: 2018).*

Jun Araya, et al. "Autophagy in the Pathogenesis of Pulmonary Disease," Internal Medicine, vol. 52, No. 20, 2013, pp. 9.

Nadia Ruocco, et al. "Blue-Print Autophagy: Potential for Cancer Treatment," Marine Drugs, 14, 138, 2016, doi:10.3390/md14070138, pp. 17.

William T. Jackson, et al.," Subversion of Cellular Autophagosomal Machinery by RNA Viruses," PLoS Biology, vol. 3, Issue 5, May 2005, pp. 11.

Nayeli Shantal Castrejon-Jimenez, et al. "The role of autophagy in bacterial infections," BioScience Trends, vol. 9, No. 3, 2015, pp. 11.

David E. Harrison, et al. "Rapamycin fed late in life extends lifespan in genetically heterogeneous mice," Nature, vol. 460, doi:10.1038/nature08221, Jul. 2009, pp. 5.

* cited by examiner

*Primary Examiner* — My-Chau T. Tran

(74) *Attorney, Agent, or Firm* — Oblon, McClelland, Maier & Neustadt, L.L.P.

(57) ABSTRACT

The present invention provides a method of inducing autophagy, the method including administering to a subject an effective amount of a pyrroloquinoline quinone compound or a salt thereof.

4 Claims, No Drawings

METHOD OF INDUCING AUTOPHAGY

BACKGROUND

Field

The present invention relates to an autophagy induction method that uses a pyrroloquinoline quinone.

Description of Related Art

Autophagy is one of the mechanisms by which components are degraded within a cell. It is a global term for a system in which components present in the cytoplasm are moved to an autophagosome (lysosome), which is a digestive organelle, and are degraded. Autophagy is a mechanism by which, under starvation conditions, the cell engages in self-digestion for the purpose of reutilization. An organism must maintain homeostasis by preserving an equilibrium between cell growth and cell death. Autophagy is related to this homeostasis.

Autophagy is understood as a cellular function that operates in particular in the reutilization of amino acids. With cultured cells, it is known that autophagy is induced in cells when culture is carried out on a culture medium for which the amino acids in the culture medium are deficient (Jun Araya, Hiromichi Hara, Kazuyoshi Kuwano, Internal Medicine Vol. 52 (2013), No. 20, pp. 2295-2303). Autophagy resists starvation conditions and is crucial for cell survival; in, for example, yeast, the cells quickly die when autophagy is inhibited and starvation conditions are imposed. In this case, autophagy can also be regarded as a mechanism that acts to prolong cell life.

A number of pathological conditions in which autophagy is implicated have been reported (N. Ruocco, Susan Costantini, and Maria Costantini, Mar. Drugs 2016, 14, 138; doi:10.3390/md14070138). In addition, autophagy also has an important action in relation to infections of exogenous pathogenesis. For example, it has been reported that autophagy is involved in the elimination of bacteria or viruses infected into the cytoplasm (Jackson W T, et al., PLoS Biol. 2005 May, 3(5), e156. Epub 2005 Apr. 26; Nayeli Shantal Castrejón-Jiménez, Kahiry Leyva-Paredes, Juan Carlos Hernández-González, Julieta Luna-Herrera, Blanca Estela García-Pérez, BioScience Trends, Vol. 9 (2015), No. 3, pp. 149-159).

It is expected that, if autophagy can be induced, this would then enable, for example, an inhibition of inflammation and defense against infection by pathogens. A strengthening of natural immunity is thought to be a characteristic feature of autophagy. Beverage and food products and drugs that have an autophagy-inducing action are little known.

Rapamycin is known to be a substance that produces autophagy. Rapamycin is an antibiotic of microbial origin and has an immunosuppressing effect. However, rapamycin is not stable and the implementation of special processing is required for its ingestion (David E. Harrison, Randy Strong, Zelton Dave Sharp, James F. Nelson, Clinton M. Astle, Kevin Flurkey, Nancy L. Nadon, J. Erby Wilkinson, Krystyna Frenkel, Christy S. Carter, Marco Pahor, Martin A. Javors, Elizabeth Fernandez & Richard A. Miller, Rapamycin fed late in life extends lifespan in genetically heterogeneous mice, Nature 460, 392-395 (16 Jul. 2009)|doi: 10.1038/nature08221.). In addition, the drug is a prescription drug and is not a material that can be generally prepared.

Pyrroloquinoline quinone is referred to as PQQ, and pyrroloquinoline quinone disodium salt is in actual use as a food product. This substance is known to be a substance that improves brain function and has an antioxidation activity (WO 2011/007633). Pyrroloquinoline quinone is the substance of formula 1.

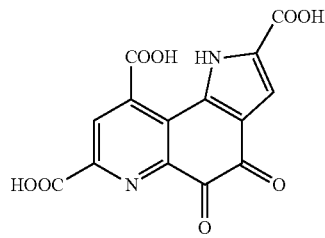

formula 1

The relationship of this substance to autophagy is unknown.

Food products, compositions, and methods that can induce autophagy are required, but a component usable in food products and able to induce autophagy by itself is unknown.

SUMMARY

The object of the present invention is to provide a method of inducing autophagy.

The present inventor carried out investigations into a variety of compounds in order to solve the aforementioned problem and discovered that pyrroloquinoline quinone induces autophagy and thus achieved the present invention.

Thus, the present invention encompasses the following embodiments.

[1] A method of inducing autophagy in a subject, the method comprising administering to the subject an effective amount of a pyrroloquinoline quinone compound or a salt thereof.

[2] The method according to [1], wherein the pyrroloquinoline quinone compound is at least one of any of the compounds of the following general formulae:

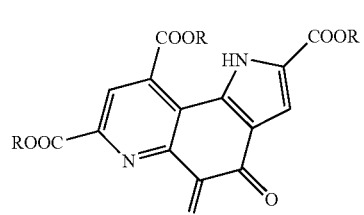

general formula (2)

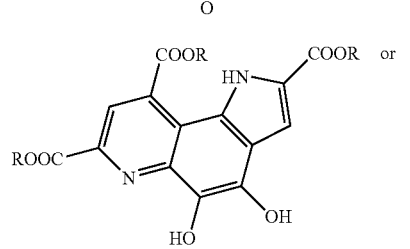

general formula (3)

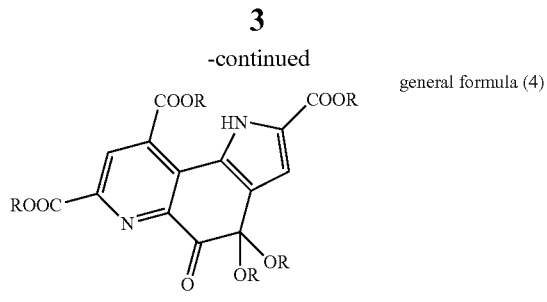

and/or a salt thereof, wherein each R in the general formulae independently is a hydrogen atom or a hydrocarbon group having 1 to 10 carbon atoms.

[3] The method according to [1], wherein the salt is a sodium salt.

[4] The method according to [1], wherein the pyrroloquinoline quinone compound is of general formula (4) and wherein at least one R is methyl.

[5] The method according to [1], wherein the subject is in need of nutritional reinforcement, activation of natural immunity, or activation of an antiinflammatory activity.

[6] A kit comprising an effective amount of a pyrroloquinoline quinone compound or a salt thereof.

The present invention can thus provide, inter alia, a method that utilizes the high autophagy-inducing action of pyrroloquinoline quinone.

DETAILED DESCRIPTION

Pyrroloquinoline Quinone and Derivatives Thereof

The method according to the present invention includes a step of administering to a subject as an effective component broadly a pyrroloquinoline quinone compound and particularly pyrroloquinoline quinone or a derivative thereof. The pyrroloquinoline quinone compounds that can be used for autophagy induction are described in detail herebelow. As used herein, pyrroloquinoline quinone compound denotes a compound that has the same main structure as pyrroloquinoline quinone and that has an antioxidation activity to the same degree as pyrroloquinoline quinone. The pyrroloquinoline quinone and derivatives thereof are not particularly limited and can be exemplified by compounds of the following general formulae (2), (3), and (4) and by salts thereof. In the Specification of this application, pyrroloquinoline quinone and its derivatives are also collectively referred to simply as "pyrroloquinoline quinone".

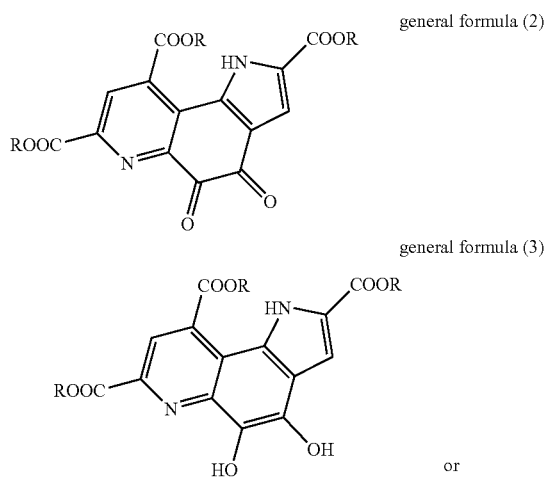

In these general formulae (2), (3), and (4), each R independently is a hydrogen atom or a hydrocarbon group having a straight chain or branched chain with 1 to 10 carbon atoms, and R is a hydrocarbon group having 1 to 10 carbon atoms.

The hydrocarbon group having a straight chain or branched chain with 1 to 10 carbon atoms and represented by R is not particularly limited and can be exemplified by alkyl and allyl. Among these, and based on considerations of ease of synthesis, straight-chain alkyl having 1 to 3 carbon atoms and particularly 1 to 2 carbon atoms is preferred. In addition to the ease of synthesis consideration, R is more preferably methyl because the water solubility can then be maintained. The hydrocarbon group having 1 to 10 carbon atoms and represented by R may contain—in addition to the carbon atom—the oxygen atom, nitrogen atom, hydrogen atom, sulfur atom, and phosphorus atom.

Compounds with General Formula (2) and Salts Thereof

The compound in which all of the R's in general formula (2) are hydrogen atoms, is known as oxidized-form pyrroloquinoline quinone. The salt of this oxidized-form pyrroloquinoline quinone is not particularly limited and can be exemplified by the tricarboxylic acid, the disalt of the tricarboxylic acid, the monosalt of the tricarboxylic acid, and the trisalt of the tricarboxylic acid. The salt is not particularly limited and can be exemplified by alkali metal salts such as the lithium salt, sodium salt, and potassium salt; alkaline-earth metal salts such as the calcium salt, strontium salt, and barium salt; and salts with cationic compounds such as the ammonium salt and alkylammonium salt.

At least one R in general formula (2) is preferably a hydrogen atom. The compound in which at least one R is a hydrogen atom, forms a salt in solution to become ionic, thus setting up a tendency to have a better water solubility than the tricarboxylic acid form.

The compound with general formula (2) and salt thereof are not particularly limited and can be exemplified by oxidized-form pyrroloquinoline quinone and alkali metal salts of oxidized-form pyrroloquinoline quinone such as oxidized-form pyrroloquinoline quinone monosodium salt, oxidized-form pyrroloquinoline quinone disodium salt, oxidized-form pyrroloquinoline quinone trisodium salt, oxidized-form pyrroloquinoline quinone dipotassium salt, and oxidized-form pyrroloquinoline quinone tripotassium salt. Among these, the sodium salts of oxidized-form pyrroloquinoline quinone, such as oxidized-form pyrroloquinoline quinone monosodium salt, oxidized-form pyrroloquinoline quinone disodium salt, and oxidized-form pyrroloquinoline quinone trisodium salt, are preferred from the standpoint of ease of acquisition.

Compounds with General Formulae (3) and (4) and Salts Thereof

Compounds with general formulae (3) and (4) in which all of the R's are hydrogen atoms, are referred to as reduced-form pyrroloquinoline quinone, which is provided by the reduction of oxidized-form pyrroloquinoline quinone. The salts of reduced-form pyrroloquinoline quinone are not particularly limited and can be exemplified by the tricarboxylic acid, disalt of the tricarboxylic acid, monosalt of the tricarboxylic acid, and trisalt of the tricarboxylic acid. The salt is not particularly limited and can be exemplified by alkali metal salts such as the lithium salt, sodium salt, and potassium salt; alkaline-earth metal salts such as the calcium salt, strontium salt, and barium salt; and salts with cationic compounds such as the ammonium salt and alkylammonium salts.

Compounds in which at least one R in general formula (3) or (4) is a hydrogen atom, form a salt in solution to become ionic. Due to this, a tendency is set up whereby the salt form has a better water solubility than the tricarboxylic acid form.

The compounds with general formulae (3) and (4) and salts thereof are not particularly limited and can be exemplified by reduced-form pyrroloquinoline quinone and alkali metal salts of reduced-form pyrroloquinoline quinone such as reduced-form pyrroloquinoline quinone monosodium salt, reduced-form pyrroloquinoline quinone disodium salt, reduced-form pyrroloquinoline quinone trisodium salt, reduced-form pyrroloquinoline quinone dipotassium salt, and reduced-form pyrroloquinoline quinone tripotassium salt. Among the preceding, the reduced-form pyrroloquinoline quinone sodium salts, such as reduced-form pyrroloquinoline quinone monosodium salt, reduced-form pyrroloquinoline quinone disodium salt, and reduced-form pyrroloquinoline quinone trisodium salt, are preferred from the standpoint of the ease of production.

At least one or more R in general formula (4) is preferably methyl. R being methylated is not particularly limited, but the hemiacetal, in which either one of the R's constituting the alkoxy groups in the quinone moiety is methyl, or the acetal, in which both of the R's constituting the alkoxy groups in the quinone moiety are methyl, is preferred.

Pyrroloquinoline quinone has a high safety, and its safety as a food ingredient has been confirmed, for example, in oral intake tests in rats, genotoxicity tests in cells and animals, and testing in humans. However, it has surprisingly been confirmed that pyrroloquinoline quinone in which the quinone moiety is acetalated, as shown in general formula (4), has a particularly high safety.

Methods for Producing Pyrroloquinoline Quinone and Derivatives Thereof

The pyrroloquinoline quinone production method is not particularly limited and can be exemplified by methods that use organic chemical synthesis and by fermentation methods. Fermentation methods are, for example, methods that produce pyrroloquinoline quinone by culturing, using methanol as a carbon source, methanol-utilizing bacteria that have the ability to produce pyrroloquinoline quinone.

The pyrroloquinoline quinone derivatives, specifically, for example, pyrroloquinoline quinone esters and pyrroloquinoline quinone salts, can be synthesized by common methods using the pyrroloquinoline quinone obtained as described above as a starting material. Pyrroloquinoline quinone and its derivatives can be separated from the reaction solution and purified by common methods, e.g., column chromatography, recrystallization, solvent extraction, and so forth. Moreover, they can be identified using various means, for example, elemental analysis, NMR spectroscopy, IR spectroscopy, mass analysis, and so forth.

The autophagy induction method of the present invention may be considered for use in various applications. Effects such as organelle degradation, an antitumor action, intracellular purification, antigen presentation, and so forth can be exerted through the induction of autophagy. The method of the present invention can therefore be used for the treatment or prevention of diseases associated with abnormal autophagy, such as tumors and inflammation. For example, the autophagy induction method of the present invention can be applied to an individual requiring nutritional reinforcement and particularly to an individual requiring an autophagy-mediated activation of natural immunity or activation of anti-inflammatory activity. In another embodiment, pyrroloquinoline quinone can be incorporated, so as to enable ingestion by such individuals, into food and beverage products for which functionality is indicated, for example, food and beverage products for specified health uses, nutritional functional food and beverage products, functional epidermal food and drink products, health functional food and beverage products, special-purpose food and beverage products, nutritional supplement food and beverage products, health supplement food and beverage products, supplements, cosmetic food and beverage products, other health food and beverage products, pharmaceuticals, quasi-drugs, cosmetics, and feed.

For the autophagy induction method, the pyrroloquinoline quinone may be administered as such or the pyrroloquinoline quinone may be administered in the form of a composition. Additives such as other physiologically active components, excipients, and so forth may also be added to the composition.

The form of the composition in which the pyrroloquinoline quinone is incorporated is also not particularly limited and can be, for example, a powder, granule, tablet, capsule, jelly, and so forth. Additional processing may be performed for special forms; for example, coating may also be performed on the surface of a tablet-form composition produced by compression tableting. Moreover, a powder may be granulated into a granular form and a powder or granulated granules may be filled into and converted into capsules.

The composition used by the present invention may be used as a tablet or powder food product. Moreover, the addition to another food product may be carried out for the purpose of nutritional reinforcement. In another embodiment, the composition used by the present invention may also be used as a seasoning that is added to a food or beverage product.

The form of the food or beverage product is not particularly limited and can be exemplified by a drink, granule, tablet, capsule, paste, kneaded product, fermented food product, confection, and so forth. The following may be incorporated in such food and beverage products as appropriate: food additives such as preservatives, colorants, sweeteners, antioxidants, thickening stabilizers, emulsifiers, seasonings, antiseptics, and so forth, and natural products. Particularly preferred food and beverage products can be exemplified by autophagy-inducing soft drinks, tea, coffee, energy drinks, capsules, and tablets. The composition may also take the form of a feed.

In addition, in order to obtain a pharmaceutical product containing pyrroloquinoline quinone or a salt thereof as an effective component, preferably an orally administratable formulation, e.g., a tablet, capsule, granule, powder, syrup, and so forth, is prepared using as appropriate a pharmaceutically acceptable carrier, for example, an excipient, lubricant, diluent, binder, disintegrant, emulsifier, stabilizer, flavorant, and so forth.

The effective dose for the present invention is preferably generally 5 mg to 150 mg/day (adult). The amount of addition of pyrroloquinoline quinone is preferably 1.66 to 50 mg as the amount per single ingestion. More specifically, in the case of a 500-mL plastic beverage bottle, the amount contained therein is preferably 1.66 to 50 mg. 3 to 40 mg is more preferred. The amount contained in a capsule or tablet is also preferably 3 to 40 mg when taking one at a time. However, these values are all examples, and the dose and the amount of incorporation of the pyrroloquinoline quinone can be determined as appropriate by the person having ordinary skill in the art within a range that does not impair the desired autophagy-inducing effect. The same also applies when the subject is a nonhuman mammal and the pyrroloquinoline quinone is incorporated into feed.

EXAMPLES

The present invention is specifically described in the following using examples, but the present invention is in no way limited to or by these.

Example 1. Pyrroloquinoline Quinone Disodium Salt (Disodium 4,5-Dioxo-4,5-dihydro-1H-pyrrolo [2,3-f]quinoline-2,7,9-tricarboxylic Acid)

Pyrroloquinoline quinone disodium salt having the following structural formula (Mitsubishi Gas Chemical Company, Inc., product name: BioPQQ (registered trademark)) was used as the compound of Example 1.

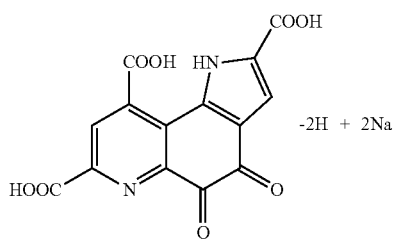 [SMILES: O=C(O)c1cc(C(=O)O)c2c(n1)C(=O)C(=O)c1cc(C(=O)O)[nH]c1-2]

Example 2. Production of the Trimethyl Ester of Pyrroloquinoline Quinone (Trimethyl 4,5-Dioxo-4,5-dihydro-1H-pyrrolo[2,3-f]quinoline-2,7,9-tricarboxylate) (PQQTME)

A large excess of hydrochloric acid was added to an aqueous solution of pyrroloquinoline quinone disodium salt and the precipitated solid was filtered off to obtain a red solid. 32 g of this solid was heated to about 30° C. in 300 g of DMF until solution was complete. 30 g of potassium carbonate was added to the resulting solution followed by mixing with 350 g of dimethyl sulfate, and after 30 minutes the temperature had risen to 50° C. due to the heat of the reaction. After lowering to room temperature, a supplementary addition of 30 g of potassium carbonate was made to the solution. The solution was stirred for 3 days at room temperature, after which 1 L of water was added and mixing with 30 g of 2 N hydrochloric acid was carried out. The reaction solution was filtered and the residue was washed with isopropanol to obtain the title compound.

Example 3. Production of Reduced-form Pyrroloquinoline Quinone (4,5-Dihydroxy-1H-pyrrolo[2,3-f]quinoline-2,7,9-tricarboxylic Acid)

3.0 g of pyrroloquinoline quinone disodium salt was dissolved in 1.2 L of water. This was mixed with 30 g of ascorbic acid, 120 g of water, and 2.5 g of 2 N hydrochloric acid, and the solution obtained by bringing the temperature to 12° C. was mixed while stirring over 2 hours with an aqueous solution of pyrroloquinoline quinone disodium salt. The pH of the mixed solution obtained by stirring for 2 hours was 2.96. After the completion of stirring, additional stirring was performed for 18 hours at 20° C. Into this was mixed 2.5 g of 2 N hydrochloric acid and stirring was performed for 1 hour. The solution was filtered on a Buchner funnel and the residue was washed with 5 mL of 2 N hydrochloric acid and 8 mL of 50% aqueous ethanol. Drying was carried out under reduced pressure for 20 hours at room temperature to obtain the title compound as 3.35 g of a yellow hydrated crystal.

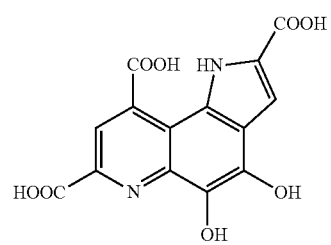 [SMILES: O=C(O)c1cc(C(=O)O)c2c(n1)c(O)c(O)c1cc(C(=O)O)[nH]c12]

Example 4. Production of Monomethylated Pyrroloquinoline Quinone (7-(Methoxycarbonyl)-4,5-dioxo-4,5-dihydro-1H-pyrrolo[2,3-f]quinoline-2,9-dicarboxylic Acid)

The title compound was synthesized as follows using the method described in Patent Publication JP-A-H5-70458, with the exception that the ethyl acetate extraction was omitted.

400 g of acetonitrile was added to 4 g of the trimethyl ester of pyrroloquinoline quinone and a solution of 5.5 g of $K_2CO_3$ dissolved in 400 g of water was also added. The obtained solution was mixed at room temperature for 2 days. 12.5 g of concentrated hydrochloric acid was added to this solution and the acetonitrile was removed with an evaporator. The precipitate was filtered off and the obtained residue was dried under reduced pressure to obtain 4.07 g of monomethylated pyrroloquinoline quinone.

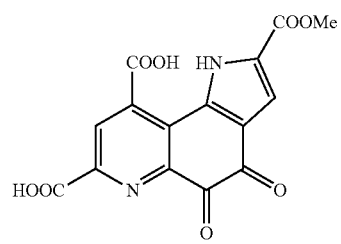 [SMILES: COC(=O)c1cc2c([nH]1)-c1c(C(=O)O)cc(C(=O)O)nc1C(=O)C2=O]

Example 5. Production of the Acetal of the Trimethyl Ester of Pyrroloquinoline Quinone (Trimethyl 4,4-Dimethoxy-5-oxo-4,5-dihydro-1H-pyrrolo[2,3-f] quinoline-2,7,9-tricarboxylate)

The compound with formula (5) was prepared based on the method described in J. Am. Chem. Soc., 1993, 115 (22), pp. 9960-9967.

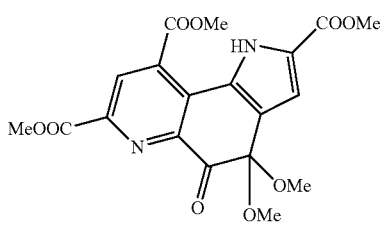

formula (5)

Evaluation of Autophagy and Method for Measuring Concentration in Relation to Cell Death The cells were cultured at 37° C. under 5% $CO_2$. The culture medium used was D-MEM (Invitrogen-Gibco) to which 10% fetal bovine serum was added.

Each of the samples from Examples 1 to 5 was mixed with water that had been sterilized at 121° C. to prepare an aqueous solution having a concentration of 2 g/L. HeLa cells were seeded to a plate at 5000 cells/well and after standing overnight the aqueous solution of 2 g/L of the substance to be evaluated was added to prepare a dilution series. After culture for 1 day, the range in which autophagy occurred was measured by fluorescence microscopic observation using a Cyto-ID (registered trademark) autophagy detection kit (Cosmo Bio Co., Ltd.). The occurrence of fluorescence was confirmed by microscopic observation, and the evaluation was carried out using as reference the same fluorescence intensity as for the rapamycin provided with the kit. Similarly, the 50% cell mortality concentration was also determined from the slope using a Cell Counting Kit-8 (Dojindo Laboratories Co., Ltd.), which is kit for measuring cell counts. The results are given in Table 1.

| | | autophagy concentration (mg/L) | 50% cell mortality concentration (mg/L) |
|---|---|---|---|
| example | | | |
| 1 | pyrroloquinoline quinone disodium salt | 0.8 | 123 |
| 2 | pyrroloquinoline quinone trimethyl ester | 0.8 | 16 |
| 3 | reduced-form pyrroloquinoline quinone | 12.5 | 48 |
| 4 | monomethylated pyrroloquinoline quinone | 0.8 | 244 |
| 5 | acetal of the trimethyl ester of pyrroloquinoline quinone | 0.8 | at least 1000 |
| comparative example | | | |
| 1 | dimethyl sulfoxide | at least 1000 (autophagy is not produced) | 674 |
| 2 | water | at least 1000 (autophagy is not produced) | — |

The results in Table 1 demonstrated that pyrroloquinoline quinone induces autophagy. In addition, the cell death concentration was well removed from the pyrroloquinoline quinone concentration at which an autophagy-inducing effect was confirmed, and it could thus be concluded that the pyrroloquinoline quinone-mediated autophagy-inducing effect is highly effective from a health standpoint. In the comparative examples, autophagy is not produced and the solutions used have little effect. Among the pyrroloquinoline quinone species, the acetal of the trimethyl ester of pyrroloquinoline quinone had the lowest toxicity and was effective. The acetalation of the quinone moiety has the effect of lowering the toxicity. Carrying out an acetalation reaction on the quinone is effective for autophagy induction.

The autophagy induction method according to the present invention can raise the natural immunity in a subject and in turn can suppress inflammation.

What is claimed is:

1. A method of inducing autophagy in a subject, the method comprising administering to the subject an effective amount of a pyrroloquinoline quinone compound selected from the group consisting of

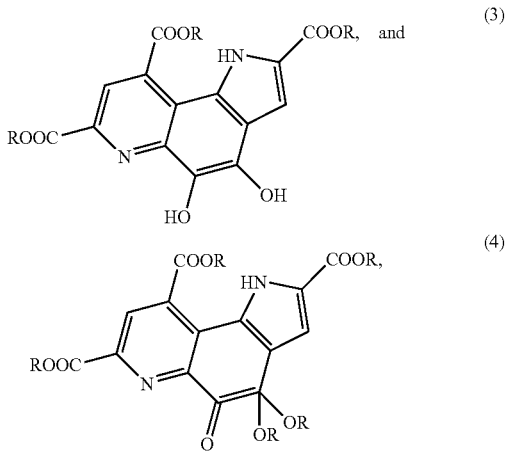

wherein each R is a hydrocarbon group having 1 to 10 carbon atoms,
or a salt thereof.

2. The method according to claim 1, wherein the salt is a sodium salt.

3. The method according to claim 1,
wherein the pyrroloquinoline quinone compound is of:

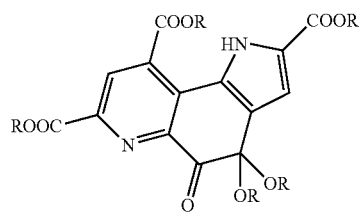

wherein at least one R is methyl.

4. The method according to claim 1,
wherein the subject is in need of nutritional reinforcement, activation of natural immunity, or activation of an antiinflammatory activity.

* * * * *